United States Patent
Broyles

[19]

[11] Patent Number: 6,095,813
[45] Date of Patent: Aug. 1, 2000

[54] METHOD FOR APPLYING A DENTAL COMPOSITION TO TOOTH STRUCTURE

[75] Inventor: Bruce R. Broyles, Oakdale, Minn.

[73] Assignee: 3M Innovative Properties Company, St. Paul, Minn.

[21] Appl. No.: 09/332,793

[22] Filed: Jun. 14, 1999

[51] Int. Cl.⁷ .......................... A61G 17/02; A61G 5/02; A61G 1/10; A61M 5/315

[52] U.S. Cl. .................. 433/80; 433/81; 433/82; 604/218

[58] Field of Search ................... 433/80, 81, 82, 433/224, 100; 604/218; 141/2, 18; 222/206

[56] References Cited

U.S. PATENT DOCUMENTS

| | | |
|---|---|---|
| D. 377,216 | 1/1997 | Mark .................................. D24/152 |
| D. 377,525 | 1/1997 | Mark .................................. D24/152 |
| 550,763 | 12/1895 | Osmun . |
| 672,207 | 4/1901 | Dunn .................................. 222/206 |
| 1,155,584 | 10/1915 | La Grange ........................... 222/206 |
| 1,533,753 | 4/1925 | Munch ................................. 222/206 |
| 2,489,035 | 11/1949 | Jones .................................. 222/206 |
| 3,230,574 | 1/1966 | Kershaw ............................... 15/563 |
| 3,345,674 | 10/1967 | Groft .................................... 15/563 |
| 3,369,543 | 2/1968 | Ronco ................................ 128/269 |
| 3,459,483 | 8/1969 | Brastad ............................... 401/131 |
| 3,464,775 | 9/1969 | Beal .................................... 401/199 |
| 3,519,364 | 7/1970 | Truhan ............................... 401/177 |
| 3,792,699 | 2/1974 | Tobin et al. ........................ 128/2 W |
| 3,818,911 | 6/1974 | Fournier ............................ 128/269 |
| 3,918,435 | 11/1975 | Beall et al. ........................ 128/2 W |
| 3,924,623 | 12/1975 | Avery ................................ 128/269 |
| 3,938,898 | 2/1976 | Reitknecht ........................ 401/183 |
| 4,225,254 | 9/1980 | Holberg et al. .................... 401/119 |
| 4,578,055 | 3/1986 | Fischer ................................. 604/2 |
| 4,969,816 | 11/1990 | Drumm ................................ 433/90 |
| 4,972,969 | 11/1990 | Randklev ............................... 222/1 |
| 4,997,371 | 3/1991 | Fischer ................................. 433/90 |
| 5,097,853 | 3/1992 | Nehashi .............................. 132/320 |
| 5,226,877 | 7/1993 | Epstein .............................. 433/100 |
| 5,246,371 | 9/1993 | Fischer ............................. 433/217.1 |
| 5,269,684 | 12/1993 | Fischer ................................. 433/90 |
| 5,283,924 | 2/1994 | Kaminski et al. .................. 15/244.1 |
| 5,286,257 | 2/1994 | Fischer ................................. 604/82 |
| 5,725,370 | 3/1998 | Himeno et al. ........................ 433/80 |
| 5,743,436 | 4/1998 | Wilcox et al. ...................... 222/137 |
| 5,755,572 | 5/1998 | Bab et al. ............................. 433/80 |
| 5,816,804 | 10/1998 | Fischer ................................. 433/90 |
| 5,846,058 | 12/1998 | Fischer ............................... 433/216 |
| 5,876,201 | 3/1999 | Wilson et al. ........................ 433/80 |

FOREIGN PATENT DOCUMENTS

| | | | |
|---|---|---|---|
| WO 89/12428 | 12/1989 | WIPO ............................. A61C 5/04 |
| WO 97/26041 | 7/1997 | WIPO ............................. A61M 37/00 |

*Primary Examiner*—John J. Wilson
*Assistant Examiner*—Robyn Kieu Doan
*Attorney, Agent, or Firm*—James D. Christoff

[57] ABSTRACT

A method of applying a dental composition to tooth structure of a dental patient includes the act of providing an applicator having an empty chamber at least partially surrounded by flexible wall portions. A tip portion of the applicator is placed into a bulk container having a quantity of dental composition, and the wall portions are squeezed together. When the wall portions are released, a portion of the dental composition is drawn into the chamber by suction. The wall portions are then squeezed together once the tip portion of the applicator has been placed next to tooth structure of a dental patient in order to dispense at least a portion of the dental composition directly onto the tooth structure. Since a sufficient amount of composition is drawn from the bulk container before the applicator is placed in the patient's oral cavity, the likelihood of cross-contamination between dental patients is substantially reduced.

12 Claims, 2 Drawing Sheets

METHOD FOR APPLYING A DENTAL COMPOSITION TO TOOTH STRUCTURE

BACKGROUND OF THE INVENTION

1. Field of the Invention

This invention relates to a method used in dental procedures for applying a composition to tooth structure. More particularly, the present invention concerns a method for applying a dental composition such as a sealant, etchant or bonding agent to a tooth or tooth preparation.

2. Description of the Related Art

Dental practitioners often apply liquid, semi-liquid and/or gel compositions to tooth structure during dental procedures. For example, bonding agents are often applied to tooth structure in order to securely fix a restoration to the tooth. Additionally, the surface of the tooth structure is often etched with an acid etchant in order to enhance the bond between the restoration and the tooth structure.

Other dental procedures also involve the application of one or more compositions to tooth structure. For example, dental sealants are often applied to the teeth to hinder the formation of caries, particularly for children. Dental sealants are available in liquid form that cures to provide a hardened protective coating for tooth enamel.

A variety of methods have been proposed in the past for applying liquid, semi-liquid or gel compositions to tooth structures. One method involves the use of a syringe having a plunger that is movable by thumb or finger pressure in order to dispense the composition through an outlet opening of a syringe tip. The tip may be guided by the practitioner across the surface of the tooth so that the composition in the syringe is dispensed directly onto the tooth structure.

Optionally, the tips of the syringes mentioned above may be provided with a plurality of fibers or bristles next to the outlet opening. As the composition is dispensed onto the tooth structure, the practitioner can move the tip in a lateral direction so that the bristles or fibers function to spread the composition over the tooth structure. The syringe tip carrying the fibers or bristles is often detachably coupled to the barrel or body of the syringe by a releasable, rotatable coupling.

Dental syringes for applying compositions to tooth structure are often supplied by the manufacturer with a quantity of composition in the syringe chamber. Typically, however, the quantity of composition in the chamber is far greater than the amount of composition needed for a single patient. As such, the syringe is often used for multiple patients, and then disposed of once the chamber is essentially empty.

When a dental syringe is used to apply composition to several patients, the syringe tip as mentioned above is typically disposed of after use with a patient and replaced with a new tip for the next patient. The syringe body is then wiped down with a disinfectant in order to reduce the likelihood of cross contamination from one patient to the next. However, there is a chance that the syringe body may not be sufficiently disinfected by such practice and provide a transfer of infectious disease from one patient to the next, which can lead to serious and possibly life threatening consequences in some instances.

Another method of applying dental compositions to tooth structure involves the use of small squeezable vials that are pre-filled with a quantity of the composition. The vials often have an angled or curved tip that enhances placement of the composition directly onto the tooth structure. The body of the vial includes flexible wall portions that, when squeezed together, dispense the composition through the tip and directly onto the tooth structure. The tip of the vial is often sealed by the manufacturer, and then cut by the practitioner to create an outlet opening through which the composition can be dispensed.

However, one known problem associated with the use of pre-filled, single use dental vials is the issue of the composition that remains in the vial after use on a single patient. Since the amount of composition needed may vary greatly in accordance with the selected procedure, the practitioner's technique in carrying out the procedure and the number of teeth involved in the procedure, such vials are typically supplied with a sufficient amount of composition to generously cover the tooth structure of the greatest number of teeth to be treated. If, for example, the practitioner need only apply the composition to one or two teeth, the amount of composition remaining in the vial is then discarded once the procedure has been completed, representing a substantial waste in some instances.

Many dental practitioners prefer to purchase dental compositions in bulk containers in order to reduce costs associated with unit dose applicators. In those instances, the practitioner will often dispense a small quantity of the composition onto a mixing well or pad, and then use a brush or swab to transfer the composition from the mixing well or pad to the patient's tooth structure. Once the procedure has been completed, the brush or swab and the mixing well or pad are disposed of or cleaned for re-use.

The practice of using a brush or swab in combination with a mixing well or pad substantially avoids problems associated with cross contamination from one patient to the next, inasmuch as the composition in the bulk container need not come into contact with the brush or swab. However, the practitioner must estimate in advance the amount of composition needed. If an insufficient amount of composition is transferred to the mixing well or pad, the practitioner will need to interrupt the procedure in order to dispense an additional amount of composition from the bulk container. On the other hand, if an excess amount of composition is dispensed into the mixing well or pad, any composition remaining at the conclusion of the procedure should not be returned to the bulk container and should be instead discarded, representing an additional waste.

As can be appreciated, there remains a need in the art for a method of applying a dental composition to tooth structure that is convenient and relatively easy to use, and yet substantially avoids the risks associated with patient cross-contamination. Preferably, such a method would be relatively inexpensive and usable with a wide variety of compositions.

SUMMARY OF THE INVENTION

The present invention overcomes the disadvantages noted above by provision of a squeezable, disposable applicator that is supplied by the manufacturer with an empty inner chamber. When desired for use, a tip portion of the applicator is inserted into a bulk container, and wall portions of the applicator are squeezed together and then released in order to draw up a quantity of composition into the chamber. The composition is then dispensed directly onto the tooth structure by squeezing the wall portions of the applicator together.

The present invention is an advantage, in that the practitioner only needs to draw up into the applicator a quantity of composition that is sufficient to coat the tooth structure of interest. For example, if only one tooth is to be treated with the composition, the practitioner may withdraw only a relatively small amount of composition from the bulk container so that little remains in the applicator once dispensed onto the tooth structure. As a result, only a small amount of composition is normally disposed of with the applicator once the procedure has been completed.

In more detail, the present invention relates to a method of applying a dental composition to tooth structure comprising the acts of providing a bulk container having a quantity of dental composition, and providing an applicator having an empty chamber at least partially surrounded by flexible wall portions. The method also includes the act of placing a portion of the tip applicator into the container and in contact with the dental composition. The method also includes the acts of squeezing the wall portions of the applicator together, and releasing the wall portions of the applicator in order to draw up a portion of the dental composition into the chamber by suction. The method further includes the acts of placing the tip portion of the applicator on tooth structure of a dental patient and squeezing the wall portions of the applicator together in order to dispense at least a portion of the dental composition directly onto the tooth structure.

These and other aspects of the invention are described in further detail below and are illustrated in the accompanying drawings.

DETAILED DESCRIPTION OF THE PREFERRED EMBODIMENTS

Figure 1:
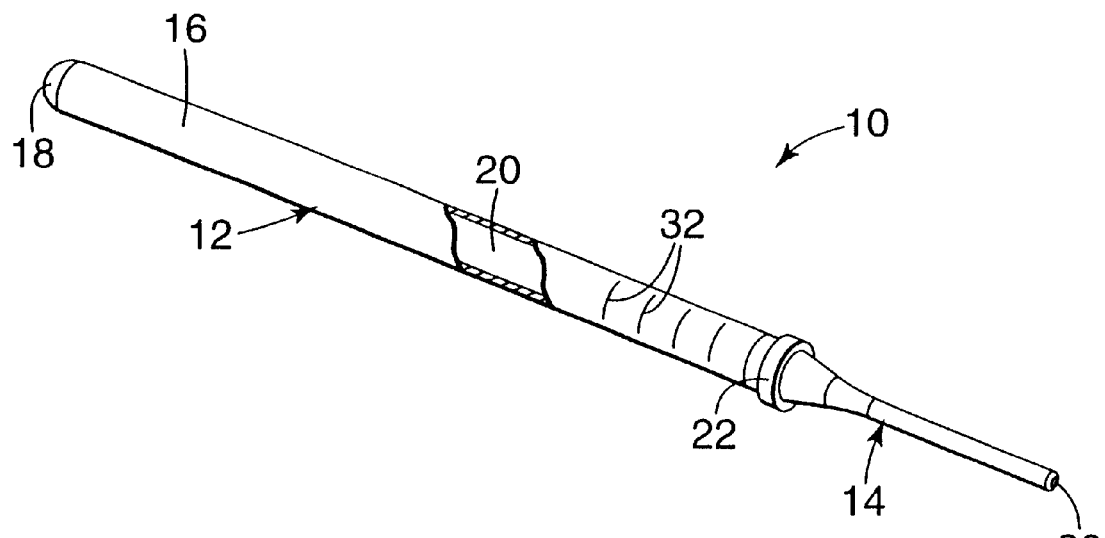
FIG. 1 is a perspective view of an applicator for dental compositions as used in one embodiment of the methods of the present invention.
Figure 2:
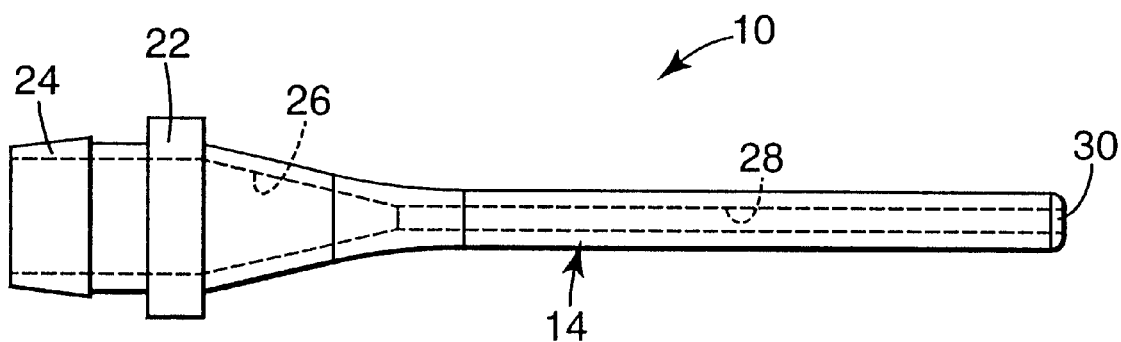
FIG. 2 is an enlarged side view of a tip portion alone of the applicator illustrated in FIG. 1.

A dental applicator for applying a dental composition to tooth structure in accordance with methods of certain embodiments of the present invention is broadly designated by the numeral 10 in FIGS. 1 and 2. The applicator 10 includes a cylindrical body 12 as well as a tip portion 14 that is connected to the body 12. The tip portion 14 is shown alone in FIG. 2.

The cylindrical body 12 has flexible side wall portions 16 that are deformable by finger pressure in lateral directions toward a longitudinal, central axis of the body 12. The body 12 also includes an outer, sealed end 18 that is preferably integrally connected to the side wall portions 16. The body 12 including the wall portions 16 and the end 18 are preferably made from a material that is resilient and inert to dental compositions. A suitable material is polypropylene but a variety of other materials may be used as well.

The body 12 is hollow and presents as inner, generally cylindrical chamber 20 for receiving a quantity of dental composition. The body 12 has an open end that is remote from the end 18. The open end is connected to the tip portion 14.

The tip portion 14 includes a coupler 22 for securely connecting the tip portion 14 to the open end of the body 12. The coupler 22 as shown in FIG. 2 has an outer flange 24 in the nature of an annular barb that is received in the body 12 adjacent its open end. The flange 24 presents an interference fit with inner surfaces of the side wall portions 16 in order to securely fix the tip portion 14 to the body 12. Optionally, a quantity of an adhesive may be applied to the coupler 22 in order to increase the strength of the bond between the tip portion 14 and the body 12.

The tip portion 14 has an internal passageway that includes a frustoconical section 26, the larger end of which has a diameter approximately equal to the diameter of the chamber 20 of the cylindrical body 12. The frustoconical section 26 narrows within the tip portion 14 to a smaller cylindrical passageway section 28 having an internal diameter that is substantially smaller than the internal diameter chamber 20. The passageway section 28 leads to an outlet opening 30 that is located on a forward end of the applicator 10.

The tip portion 14 is preferably made of a relatively inexpensive material such as polypropylene or polyethylene. Optionally, the tip portion 14 is bendable in an arc by the user to any one of a number of different configurations in order to enhance access to certain tooth structure, especially tooth structure that is located in posterior regions of the patient's dental arch. When the tip portion 14 is bent in such a manner, the outer, forward end of the passageway section 28 extends at an angle relative to the longitudinal axis of the chamber 20. During such bending, the outer section of the tip portion 14 preferably is deformed past its yield point in order to better retain its shape during a subsequent dispensing operation.

A variety of other constructions are also possible. For example, a number of other couplers may be substituted for the coupler 22. Examples of suitable couplers include threaded couplers, bayonet-type locking couplers and couplers having sliding, telescoping sections that matingly fit with each other. Such couplers could be joined together with adhesive or by other means if desired.

Other possible constructions for the applicator 10 include one-piece constructions, wherein the body and the tip portion are integrally molded together and the coupler is omitted. In such construction, the applicator could be initially molded with an open rear end that is later sealed shut in order to close the rear end of the chamber. Other alternative applicators include applicators having slender, needle-like tip portions made of a metal cannula.

A method of applying a dental composition to tooth structure using the applicator 10 includes the act of providing a bulk container having a quantity of dental composition. The bulk container is not shown in the drawings but could be any suitable container, such as a bottle or a vial that holds a sufficient amount of composition for use with several dental patients. The dental composition could be any liquid, semi-liquid or relatively low-viscosity gel material. Suitable compositions include dental etchants, dental sealants and dental bonding agents (such as primers and adhesives), periodontal medicaments and tooth whitening agents, although other dental compositions may be used as well.

Next, the outlet opening 30 of the applicator 10 is placed into the bulk container and in contact with dental composition in the bulk container. The flexible wall portions 16 are then squeezed together by the user's fingers. Subsequently, finger pressure on the wall portions 16 is released and the wall portions 16 self-deflect outwardly under their inherent memory to return to their normally cylindrical configuration. As the wall portions 16 are released, a slight negative pressure is established in the chamber 20 that tends to draw up a portion of the dental composition from the bulk container and into the chamber 20 by suction.

Subsequently, the tip portion 14 of the applicator 10 is removed from the confines of the bulk container and is placed on tooth structure of a dental patient. The practitioner then squeezes the flexible wall portions 16 together by finger pressure. As the wall portions 16 move inwardly, the volume of the chamber 20 is reduced and a portion of the dental composition is directed outwardly through the passageway sections 26, 28 and out the outlet opening 30, and preferably directly onto the tooth structure of the patient.

Preferably, and as illustrated in FIG. 1, the body 12 is provided with a series of index marks 32 to enable the practitioner to determine the amount of dental composition that is drawn into the chamber 20. Preferably, each index mark 32 corresponds to an appropriate amount of the dental composition contained in the chamber 20 for application to a single tooth. For example, if the level of the dental composition in the chamber 20 reaches the third index mark when the applicator 10 is oriented in a vertical direction with the outlet opening 30 facing downwardly, the practitioner can assume that there is sufficient composition in the chamber 20 for application to three of the patient's teeth.

The method as described above is a significant advantage over past practices, because the applicator 10 may be used to withdraw dental composition directly from the bulk container without transfer to an intermediate location such as a mixing well or the like. The index marks 32 enable the practitioner to know in advance whether or not a sufficient quantity of composition has been withdrawn from the bulk container into the chamber for the particular dental procedure to be undertaken. If the quantity is insufficient and the level of composition does not reach the desired index mark, an additional amount of the composition can be drawn into the chamber 20 before the dispensing operation begins. As a consequence, the applicator 10 only contacts the composition in the bulk container before the applicator 10 is used in the patient's oral cavity, such that issues of cross-contamination are avoided and the risk of transferring an infectious disease from one patient to another is substantially reduced.

Use of the applicator 10 represents a time savings for the practitioner since the composition is contained in the applicator 10, and repeated refillings are not needed for a dental procedure. In contrast, the use of a brush or swab often requires the practitioner to dip the brush or swab in the mixing well or on the mixing pad numerous times during the course of a procedure to obtain additional composition, and such repeated, back-and-forth movements between the oral cavity and the mixing well or pad can lengthen the time needed for the procedure.

Furthermore, the method in accordance with the present invention reduces waste of the composition, since the practitioner only needs to withdraw sufficient composition from the bulk container into the chamber 20 for the desired dental procedure. Once the procedure has been completed, only a relatively small amount of the composition remains in the applicator 10 and the applicator 10 is disposed of in a suitable manner. A new, empty applicator (such as another applicator similar to applicator 10) is used with a subsequent patient, so that again only a new uncontaminated applicator is ever placed within the confines of the bulk container.

The applicator 10 provides other advantages as well. For example, if an excess amount of material is applied to the tooth surface, the practitioner can squeeze the wall portions 16 together and then release the wall portions 16 while placing the outlet opening 30 on the excess composition in order to withdraw some of the composition from the tooth structure and back into the chamber 20.

Additionally, the applicator 10 can be used to remove bubbles when certain compositions such as sealants are applied to the patient's teeth. Bubbles in sealants are a particular nuisance, and often result in the practitioner attempting to pop the bubble with an explorer or attempting to wipe off the sealant and then reapply the sealant as a new coating. In accordance with the present invention, the flexible wall portions 16 can be squeezed together while the outlet opening 30 is placed adjacent the bubble and the bubble can then be removed by suction when the finger pressure on the wall portions 16 is released.

The method of the present invention is also an advantage in that the applicator 10 is relatively small in size and easy to maneuver in the confines of a relatively small oral cavity of a younger patient. The flexible wall portions 16 provide good tactile feedback for the practitioner, and enable the applicator 10 to be firmly gripped while maneuvered to a precise location in the oral cavity. The grip on the applicator 10 is a particular advantage in comparison to the grip necessary to hold and operate syringe-type applicators having a rear plunger. Moreover, the applicator 10 has the appearance of a brush and does not appear as intimidating to younger patients in comparison to, for example, syringe-type applicators or gun-type applicators.

Figure 3:
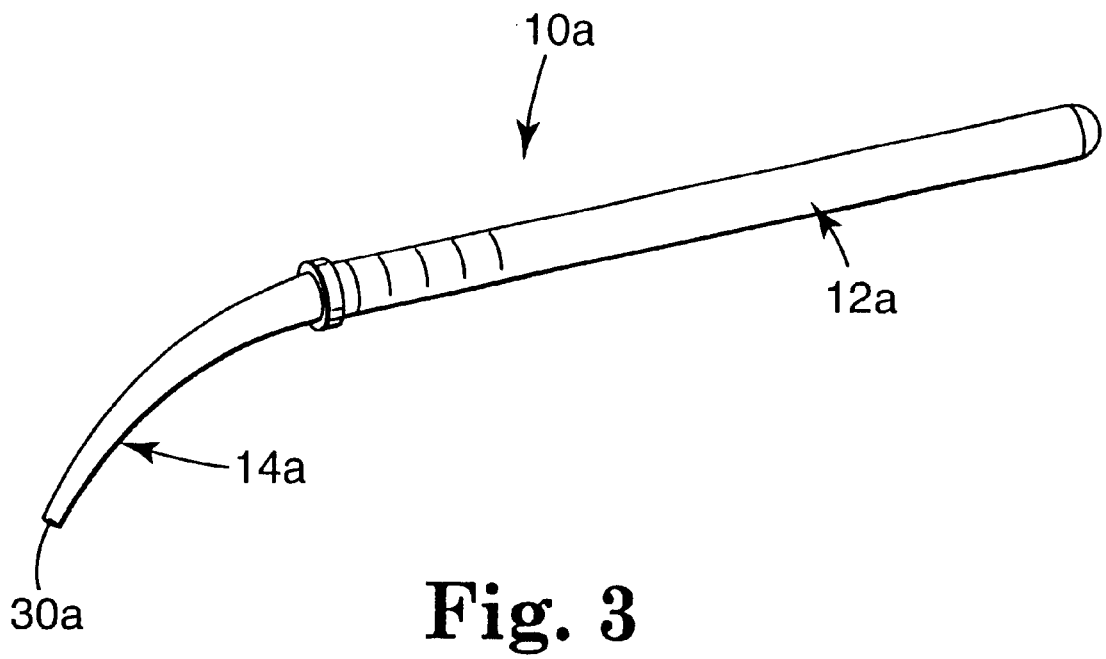
FIG. 3 is a perspective view of a dental applicator used in methods according to another embodiment of the invention.

A dental applicator 10a according to another embodiment of the invention is illustrated in FIG. 3. The applicator 10a includes a cylindrical body 12a that is the same as the cylindrical body 12 described above, and a tip portion 14a that is essentially the same as the tip portion 14 with the exceptions noted below.

The tip portion 14a has an internal passageway which gradually narrows as an outer, outlet opening 30a is approached. Thus, instead of a frustoconical passageway section and a cylindrical passageway section, the passageway of the tip portion 14a has an internal diameter that smoothly and steadily decreases as the outlet opening 30a is approached. Such construction is an advantage for certain dental compositions, especially for dental compositions having a relatively high viscosity.

Additionally, the tip portion 14a has a curved central longitudinal axis as illustrated in FIG. 3. Preferably, the curve is made by the manufacturer. As such, the user need not bend the tip portion 14a for use in many dental procedures. The curved central axis of the tip portion 14a facilitates access in certain areas of the oral cavity such as the posterior regions of the patient's upper and lower dental arches.

Other features and aspects of the applicator 10a are the same as the corresponding features and aspects of the applicator 10, and need not be described again in detail.

Figure 4:
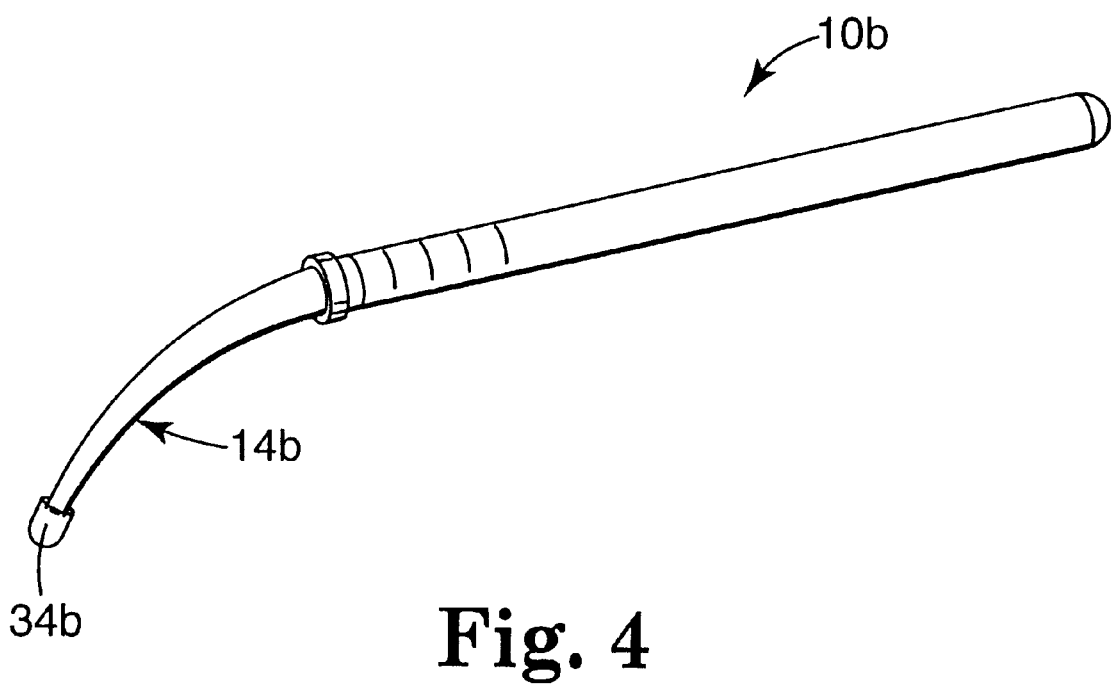
FIG. 4 is a perspective view of a dental applicator used in other methods according to an additional embodiment of the present invention.

An applicator 10b for applying a dental composition to tooth structure according to another embodiment of the invention is shown in FIG. 4. The applicator 10b is essentially the same as the applicator 10a, except that the applicator 10b includes a tip portion 14b that has a quantity of material 34b surrounding its outlet opening. The material 34b facilitates spreading of the dental composition across the tooth structure as the dental composition is dispensed from an inner chamber of the applicator 10b.

The material 34b may be any suitable structure that is compatible with the dental composition and functions to spread the composition over the tooth structure. Suitable materials include small bristles or fibers that serve as a brush. The fibers or bristles could be arranged to surround the outlet opening or could instead be placed along one side of the outlet opening as desired.

Optionally, fibers can be applied to the tip portion 14b by a flocking process. The flocking can be applied by any known or developed technique, such as is done in making the flocked tip disposable applicators that are commercially available from Microbrush Corporation of Clearwater, Florida under the trade designation "Microbrush." The flocked fibers define small interstitial spaces that can advantageously fill with the composition, and retain and suspend a small amount of the composition after it has been dispensed from outlet 30 to provide for efficient application to a preparation site. The fibers also allow relatively uniform application of the composition over the surface(s) of the preparation site, whether irregular, rough, or smooth, and apply the composition in the same way as a brush would. In a tooth cavity, the outwardly extending fibers permit the composition to be applied easily to side and overhang surfaces of the tooth cavity as well as the cavity bottom.

Other suitable materials for spreading the composition across the tooth structure include an open cell foam material such as a polyurethane foam or synthetic sponge. Suitable materials also include woven and non-woven fabrics, gauzes and the like. Microstructured surfaces could also be employed.

The methods as described above in the various embodiments are illustrative of the invention and are presented to point out many of the features and advantages of the invention in comparison to past practices. Those skilled in the art will recognize that a number of variations and modifications are possible to the acts described in detail above without departing from the spirit of the invention. Consequently, the invention should not be deemed limited to the specific acts described above, but instead only by a fair scope of the claims that follow along with their equivalents.

I claim:

1. A method of applying a dental composition to tooth structure comprising the acts of:

providing a bulk container having a quantity of dental composition;

providing an applicator having an empty chamber at least partially surrounded by flexible wall portions;

determining an amount of dental composition needed for a complete dental procedure;

placing a tip portion of the applicator into the container and in contact with the dental composition;

squeezing the wall portions of the applicator together;

releasing the wall portions of the applicator in order to draw up a portion of the dental composition into the chamber by suction, wherein the portion drawn into the chamber is an amount sufficient for the dental procedure;

placing the tip portion of the applicator next to tooth structure of a dental patient;

squeezing the wall portions of the applicator together in order to dispense at least a portion of the dental composition directly onto the tooth structure; and disposing of the application after at least a portion of the dental composition is dispensed onto both structure so that the tip portion of the applicator is not placed back into the container.

2. The method of claim 1 wherein the tip portion of the applicator has a curved longitudinal axis.

3. The method of claim 1 wherein the flexible wall portions have a generally cylindrical configuration.

4. The method of claim 1 and including the act of providing the applicator with one or more index marks for determining the amount of dental composition drawn into the applicator.

5. The method of claim 4 wherein the act of providing the applicator with one or more index marks includes the act of providing an index mark that corresponds to an appropriate amount of the dental composition contained in the chamber for application to a single tooth.

6. The method of claim 1 including the act of providing the applicator with a series of index marks for determining the amount of dental composition drawn into the applicator and wherein each index mark corresponds to an appropriate amount of the dental composition contained in the chamber for application to a predetermined quantity of teeth.

7. The method of claim 1 and including the act of sliding the tip portion along the tooth structure in order to spread the dental composition on the tooth structure.

8. The method of claim 7 wherein the act of sliding the tip portion along the tooth structure includes the act of sliding a plurality of fibers along the tooth structure.

9. The method of claim 7 wherein the act of sliding the tip portion along the tooth structure includes the act of sliding a foam material along the tooth structure.

10. The method of claim 1 wherein the dental composition is a sealant, etchant or bonding agent.

11. The method of claim 1 wherein the dental composition is an agent for whitening the teeth.

12. The method of claim 1 wherein the dental composition is a medicament for periodontal treatment.

* * * * *